United States Patent [19]

Thistle et al.

[11] Patent Number: 4,793,776
[45] Date of Patent: Dec. 27, 1988

[54] PUMP FOR OSCILLATING A FLUID IN VIVO

[75] Inventors: Johnson L. Thistle, SW. Rochester; Patrick E. Caskey, Rochester; Wayne H. Fjerstad, Mantorville, all of Minn.

[73] Assignee: Research Corporation, New York, N.Y.

[21] Appl. No.: 130,134

[22] Filed: Dec. 8, 1987

Related U.S. Application Data

[62] Division of Ser. No. 773,404, Sep. 6, 1985, Pat. No. 4,723,941.

[51] Int. Cl.[4] .............................................. F04B 39/14
[52] U.S. Cl. ..................................... 417/360; 417/415
[58] Field of Search ............... 417/305, 319, 360, 385, 417/415, 423 F, 423 L, 423 T, 435, 439, 442, 434, 503; 604/31, 120, 152; 60/537, 594; 92/17, 128; 74/89.15

[56] References Cited

U.S. PATENT DOCUMENTS

| | | |
|---|---|---|
| 3,426,743 | 2/1969 | Chestnut et al. . |
| 3,556,679 | 1/1971 | Middlebuster et al. ......... 417/415 X |
| 3,771,918 | 11/1973 | Winter ........................... 417/319 X |
| 3,958,903 | 5/1976 | Capelli ............................... 417/503 |
| 4,221,548 | 9/1980 | Child . |
| 4,255,096 | 3/1981 | Coker, Jr. et al. ................... 417/415 |
| 4,284,073 | 8/1981 | Krause et al. . |
| 4,315,506 | 2/1982 | Kayser et al. . |
| 4,336,000 | 6/1982 | Jorgensen et al. .............. 417/435 X |
| 4,493,614 | 1/1985 | Chu et al. ....................... 417/415 X |
| 4,526,575 | 7/1985 | Roblejo . |
| 4,673,296 | 6/1987 | Sjogren ........................... 417/503 X |

FOREIGN PATENT DOCUMENTS 181012 2/1955 Austria .
1823012 8/1960 Fed. Rep. of Germany .

OTHER PUBLICATIONS

*Gastroenterology*, vol. 78, No. 5, 1980, pp. 1016–1022, J. L. Thistle, et al.

Primary Examiner—Carlton R. Croyle
Assistant Examiner—Eugene L. Szczecina, Jr.
Attorney, Agent, or Firm—Scully, Scott, Murphy & Presser

[57] ABSTRACT

A pump for oscillating a fluid into and out from a body area. The pump forms a fluid chamber for holding the fluid, and comprises a piston for forcing fluid outward from the fluid chamber and into the body, and for drawing fluid inward from the body and into the fluid chamber. A motor is connected to the piston, and a control circuit is connected to the motor to control movement of the piston. The control circuit has a first state actuating the motor to force the fluid into the body, and a second state actuating the motor to draw the fluid from the body, and the control circuit may be adjusted to vary the rates at which fluid is forced into and drawn from the body.

12 Claims, 5 Drawing Sheets

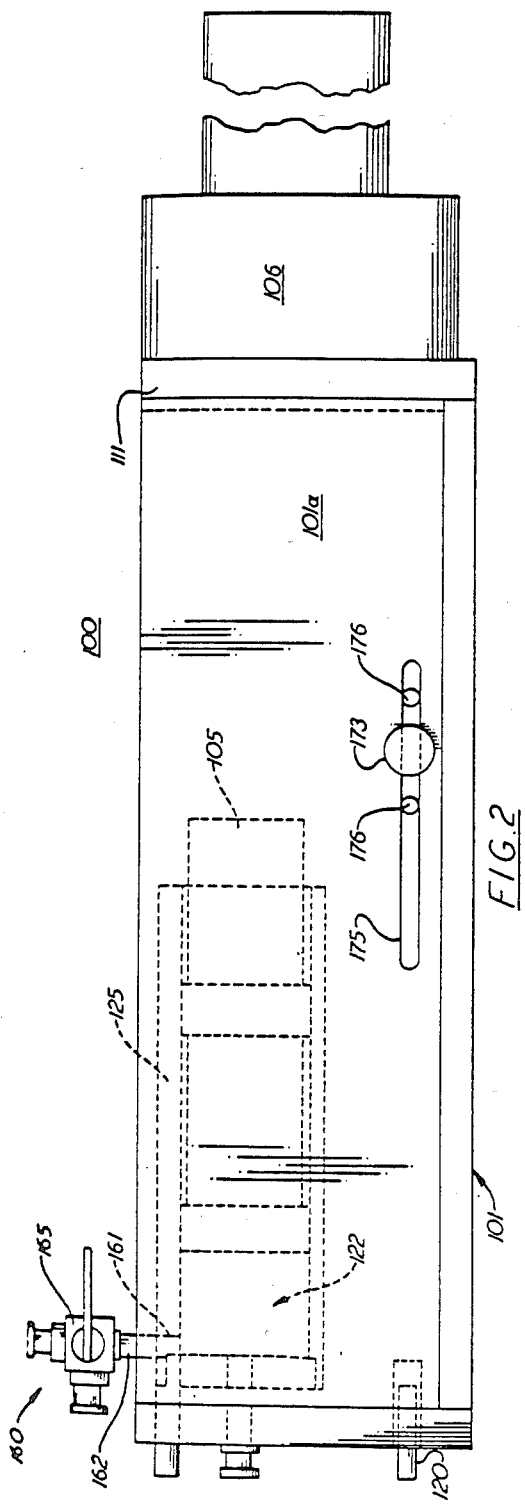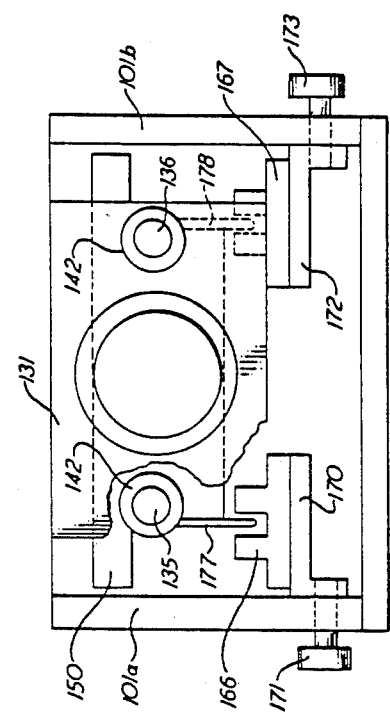

OPERATING TABLE FOR THE LOGIC SUBCIRCUIT WHEN THE PISTON IS MOVING

| PISTON | VOLTAGE LEVEL OF POINT 166c | VOLTAGE LEVEL OF POINT 167c | FLIP-FLOP 212 INPUTS a b | FLIP-FLOP 212 OUTPUTS c d | NAND GATE 215 INPUTS a b | NAND GATE 215 OUTPUTS c | NAND GATE 216 INPUTS a b | NAND GATE 216 OUTPUTS c | SWITCH 202b | SWITCH 205b |
|---|---|---|---|---|---|---|---|---|---|---|
| #1 MOVING FORWARD | 0 | 0 | 1 1 | 0 1 | 0 1 | 1 | 1 1 | 0 | OPEN | CLOSED |
| #2 AT FORWARDMOST POSITION | 1 | 0 | 0 1 | 1 0 | 1 1 | 0 | 0 1 | 1 | CLOSED | OPEN |
| #3 MOVING REARWARD | 0 | 0 | 1 1 | 1 0 | 1 1 | 1 | 0 1 | 1 | CLOSED | OPEN |
| #4 AT REARWARDMOST POSITION | 0 | 1 | 1 0 | 0 1 | 0 1 | 1 | 1 1 | 0 | OPEN | CLOSED |

FIG. 7

OPERATING TABLE FOR THE FLIP-FLOP OF THE STOP-START SUBCIRCUITS

| INPUTS a c | OUTPUT d | | MOTOR |
|---|---|---|---|
| 1 1 | 0 | d REMAINS AT 0 UNTIL START SWITCH IS CLOSED AND THEN OPENED, AND THEN d CHANGES TO 1. | OFF |
| 1 1 | 1 | d REMAINS AT 1 UNTIL EITHER a OR c CHANGE TO 0, AND THEN d CHANGES TO 0. | ON |
| 1 0 | 0 | d REMAINS AT 0 UNTIL c CHANGES TO 1, AND START SWITCH IS CLOSED AND THEN OPENED, AND THEN d CHANGES TO 1. | OFF |

0 = LOW VOLTAGE
1 = HIGH VOLTAGE

FIG. 8

PUMP FOR OSCILLATING A FLUID IN VIVO

This is a divisional of copending application Ser. No. 773,404 filed on Sept. 6, 1985, now U.S. Pat. No. 4,723,941.

BACKGROUND OF THE INVENTION

This invention generally relates to a pump for oscillating a fluid in vivo, for example, to facilitate the dissolution of solidified masses that have developed in the body.

Solidified masses such as biliary duct stones and gall stones may develop in hollow organs or ducts within humans and animals and cause numerous health problems, as is known to those skilled in the art. These deposits may be removed from the body in various ways, including surgery or in vivo dissolution of the concretion by solvents introduced into the area of the body where the solidified masses are located. The hazards and complications attributable to surgery are well known, and it is desirable to avoid surgery where suitable alternatives are available. Heretofore, however, in vivo dissolution of cholesterol calculi has been undertaken with only limited success for several reasons.

For example, the effectiveness of such an in vivo process depends, in part, on the thoroughness with which the solvent fluids diffuse throughout the area of the body being treated, and conventional methods and devices for introducing therapeutic fluids into localized body areas normally do not produce any more than a limited distribution of the fluid in that body area. Also, cholesterol calculi dissolve at a relatively slow rate when simply placed in contact with a solvent fluid. It is known that the dissolution of such solids in a solvent is normally accelerated by stirring or agitating the solvent; however, as is known by those in the art, many practical difficulties are encountered when trying to agitate a liquid in vivo.

SUMMARY OF THE INVENTION

An object of this invention is to stir a solvent fluid in a body area to increase the effectiveness of the solvent.

Another object of this invention is to oscillate a fluid into and out from a localized body area to agitate a solvent fluid in that area to improve the distribution and the effectiveness of the solvent fluid.

A further object of this invention is to inject a fluid into a localized body area at a relatively high rate and to aspirate the fluid from the body area at a slower rate.

Still another object of the present invention is to provide a pump for oscillating a fluid into and out from a body area, where the parts of the pump that come into direct contact with the oscillating fluid are easy to remove and replace.

These and other objects are attained with a pump for directing an oscillating fluid into and out from a body area. The pump comprises a member forming a pump inlet and a fluid chamber in communication therewith for holding the fluid; oscillating means for forcing fluid outward from the fluid chamber and into the body area, and for drawing fluid inward from the body area and into the fluid chamber; power means connected to the oscillating means to drive said oscillating means, and control means connected to the power means to control movement of the oscillating means. The control means includes switch means having a first state actuating the power mean to force fluid outward from the pump and into the body area, and a second state actuating the power means to draw the fluid from the body area and inward into the pump. The switch means includes first adjustable means to vary the rate at which fluid is forced into the body area, and second adjustable means to vary the rate at which fluid is draw from the body area. The control means further includes means to change the switch means between its first and second states.

BRIEF DESCRIPTION OF THE DRAWINGS

FIG. 2 is a side view of the pump shown in FIG. 1.

FIG. 3 is a front view of the pump.

FIG. 7 shows an operating table for a logic subcircuit of the electric control circuit.

FIG. 8 shows an operating table for a flip-flop of a stop-start subcircuit of the control shown in FIG. 6.

A DETAILED DESCRIPTION OF THE PREFERRED EMBODIMENTS

Figure 1:
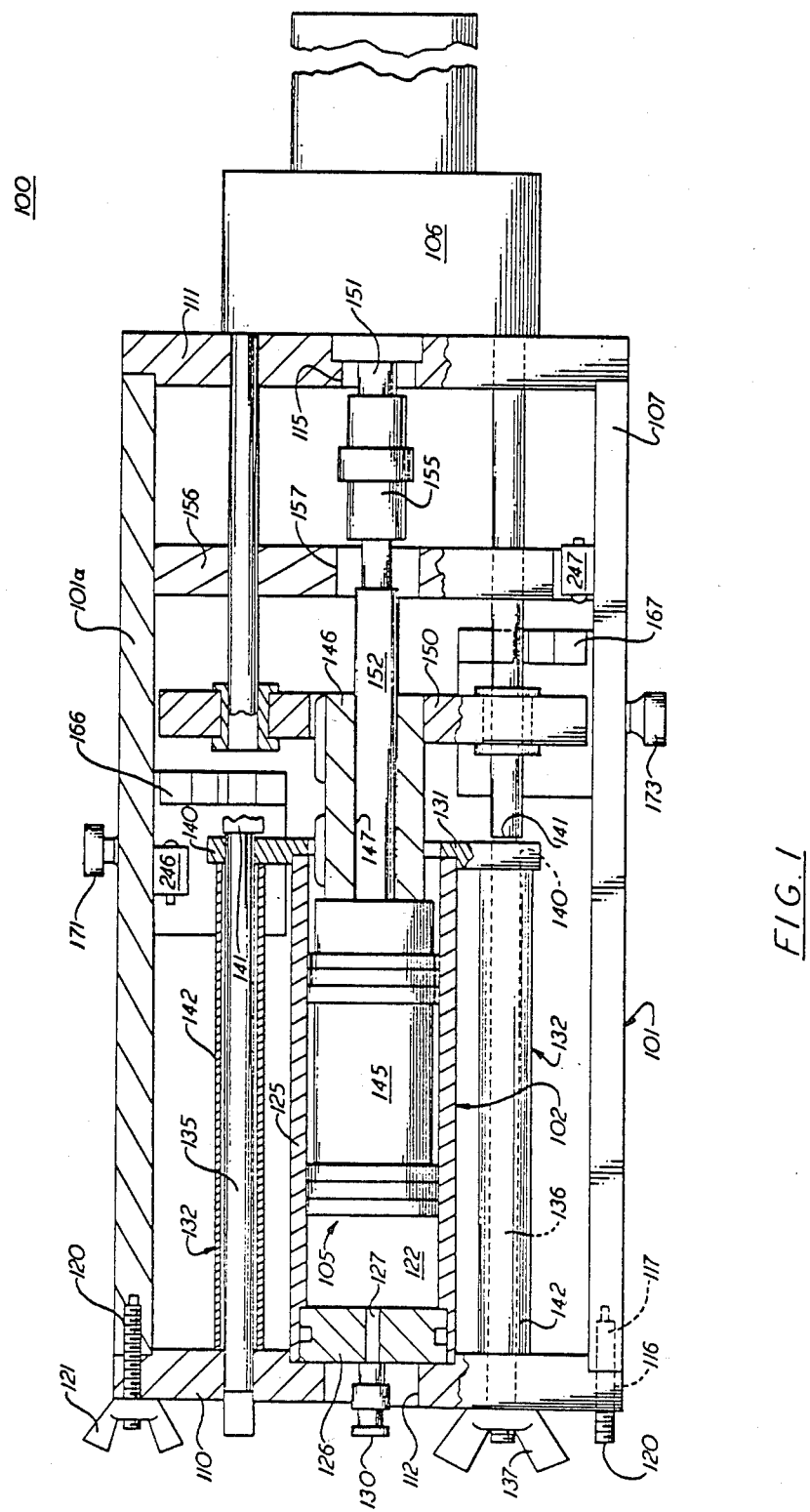
FIG. 1 is plan view, partially in cross-section, of a pump in accordance with this invention.
Figure 5:
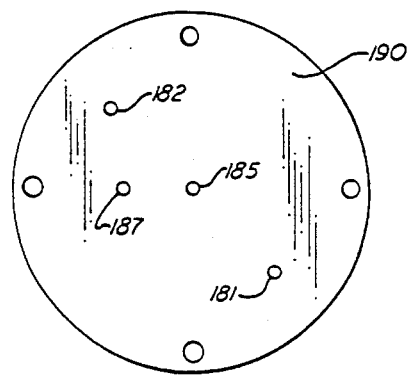
FIG. 5 is a top view of the cover of the trap.
Figure 4:
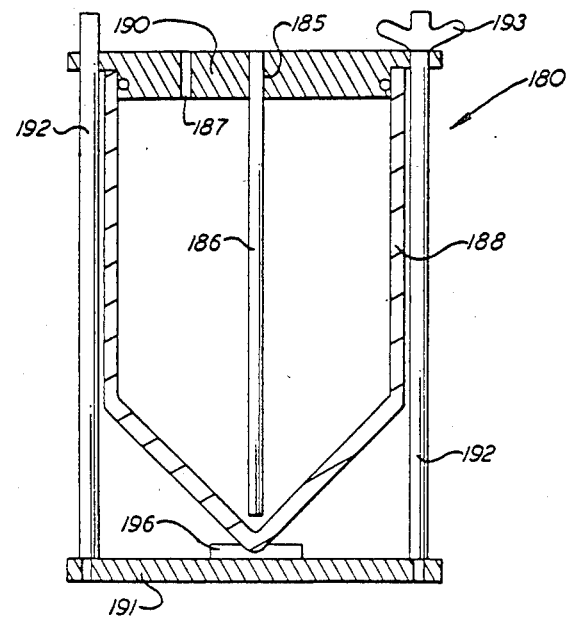
FIG. 4 is a cross-sectional view of a trap that may be used with the pump shown in FIGS. 1–3.
Figure 6:
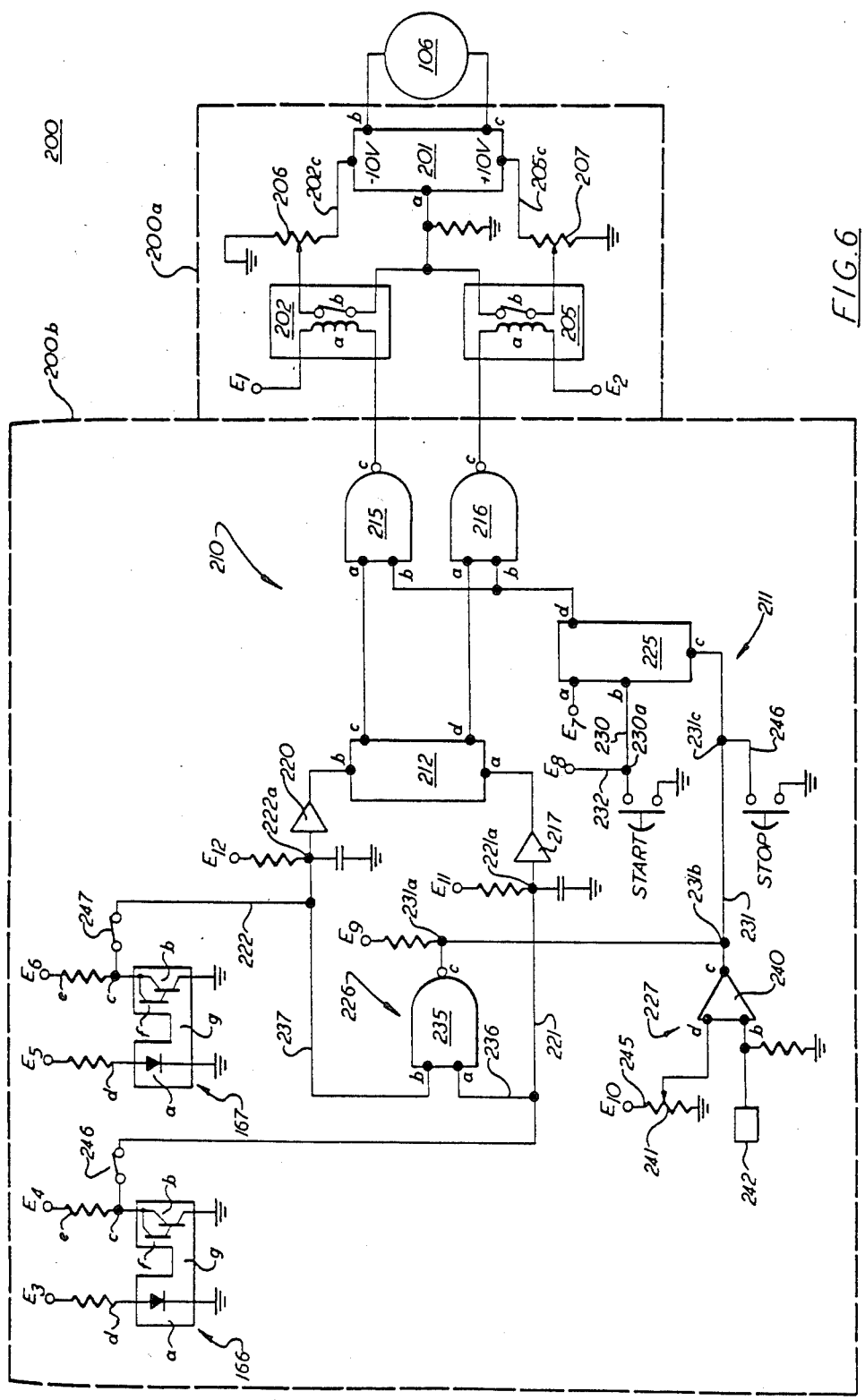
FIG. 6 is a schematic drawing of an electric control circuit for the pump.

FIGS. 1–3 illustrate a pump 100; FIGS. 4 and 5 show a trap 180 that may be used with pump 100, and FIGS. 6–8 show and summarize the operation of control circuit 200 for the pump. The structure of the pump 100 will be described first, then trap 180 will be discussed, and then control circuit 200 will be explained in detail.

Generally, pump 100 comprises support frame 101, cylinder 102, piston 105 and power means such as electric motor 106. Support frame 101 provides a protective structure or enclosure for cylinder 102 and piston 105, and preferably the support frame comprises longitudinally extending side section 107 and front and back plates 110 and 111. Side section 107 is formed of three rectangular plates having longitudinal edges connected together to form a strong frame having a U-shaped cross section. Side section 107 forms front and back openings, and plates 110 and 111 extend across these openings respectively. Front plate 110 supports cylinder 102 inside pump 100, and the front plate forms pump inlet 112 for conducting a fluid into and out from the interior of that cylinder. Back plate 111 forms opening 115 receiving a shaft of motor 106, discussed below.

The various plates of support frame 101 may be made of any suitable material and connected together in any suitable way, and the support frame may have shapes other than as illustrated in the drawings. For instance, the plates of frame 101 may be made from aluminum and screwed or bolted together to form the support frame. In use, the top of support frame 101 may be covered, for example, by a plexiglass plate screwed to top edges of the support frame. Alternately, side section 107 of support frame 101 may have a tubular or cylindrical shape.

Preferably, regardless of the specific way the other parts of support frame 101 are connected together, front plate 110 is releasably connected to side section 107. This releasable connection may be made in a variety of ways. For example, as illustrated in the drawings, front plate 110 defines a plurality of through bores 116 that are aligned with threaded sockets 117 formed in the front edges of side section 107. Pins 120, which have threaded front and back portions, extend through bores 116 and are securely threaded into sockets 117. Pins 120 extend forward of plate 110, and wing nuts 121 are threaded onto front portions of those pins and into a tight pressure fit against the front plate, holding that plate securely against front edges of side section 107.

Cylinder 102 is located inside support frame 101 and forms a fluid chamber 122 for holding a supply of the fluid that is injected into and aspirated from the body of a patient. As depicted in the drawings, cylinder 102 abuts against front plate 110 and extends rearward therefrom, and the cylinder includes tubular side wall 125 and a cylindrically shaped head or plug 126. Head 126 is inserted into a forward end of side wall 125, in a close fit therewith, and the head is captured in place between front plate 110 and an annular shoulder formed in side wall 125. Alternately, head 126 may be held in a tight frictional fit with side wall 125. Head 126 forms inlet portion 127 of fluid chamber 127, and a seal may be fitted around the circumference of the head, against side wall 125, to seal the space between the head and the tubular side wall. Head 126 and tubular side wall 125 may be formed from stainless steel, and the circumferential seal that is fitted on the outside of the head may be comprised of a pair of split Teflon washers. A catheter connection 130 may be fitted into inlet 127 to adapt pump 100 for connection to a standard catheter tube.

Cylinder 102 is connected to and held in place inside support frame 101 by connecting means generally comprising retaining plate 131 and means 132 supporting the retaining plate inside the support frame. More specifically, this support means 132 extends rearward from front plate 110; and retaining plate 131 is supported by support means 132, transversely extends across cylinder 102, rearward thereof, and captures the cylinder between the front plate and the retaining plate.

Preferably, support means 132 comprises a pair of support rods 135 and 136 extending rearward from front plate 110. More particularly, support rods 135 and 136 longitudinally extend completely across support frame 101 and rear ends of the support rods are threaded into threaded bores formed in back plate 111. Support rods 135 and 136 also extend slightly forward of front plate 110, and wing nuts 137 are mounted on the front ends of the support rods and threaded into tight pressure engagement with the front plate, holding the support rods taught between the front and back plates.

With the embodiment of the invention shown in FIGS. 1-3, retaining plate 131 forms a pair of outside openings 140 and support rods 135 and 136 extend through these openings to mount the retaining plate on those rods. Retaining plate 131 also forms a central openings 141 through which piston 105 extends. Support rods 135 and 136 form annular shoulders 141 rearward of plate 131 to limit rearward movement thereof, and spacing sleeves 142 are mounted on the support rods forward of the retaining plate to limit forward movement thereof. Preferably, retaining plate 131 is tightly captured between sleeves 142 and shoulders 141; and, in turn, cylinder 102 is tightly held between the retaining plate and front plate 110. Plates 110 and 131 may form longitudinally aligned, axial recesses that receive opposite ends of cylinder 102 to help hold the cylinder in place inside pump 100.

As will be appreciated by those of ordinary skill in the art, retaining plate 131 may be held within support frame 101 in a variety of other ways. In particular, it should be noted that the plate 131 may be longitudinally held in place by the combination of a single shoulder 141 and a single sleeve 142 formed and mounted respectively on a support rod. Retaining plate 131, rods 135 and 136, and sleeves 142 are preferably made from aluminum, although other materials may be used.

Piston 105 extends into cylinder 102 and is supported therein for forward and rearward reciprocating movement to force fluid outward from chamber 122 and into the patient and to aspirate fluid from the patient and into chamber 122. More particularly, piston 105 has a generally cylindrical shape, and extends into fluid chamber 122 in a close sliding fit with the inside surfaces of tubular side wall 125. One or more outside circumferential seals may be seated on piston 105 to seal the annular gap between the piston and cylinder 102. Piston 105 may be made from stainless steel, and the seals that are mounted on the piston may be comprised of pairs of split Teflon washers. Piston 105 shown in FIG. 1 includes axially aligned front, or head, section 145 and back, or driving, section 146. Driving section 146 comprises a conventional screw nut, and a rear portion of head section 145 is threaded onto a forward portion of this screw nut so that the two sections of piston 105 longitudinally move together inside support frame 101. Screw nut 146 forms a longitudinally extending threaded bore 147 and is supported in pump 100 in a manner that prevents rotation of the screw nut. For instance, bar 150 may be mounted on support rods 135 and 136 and connected to screw nut 146 of piston 105 by one or more set screws to prevent rotation of the screw nut and, thus, of the piston relative to support frame 101.

Motor 106 is secured to support frame 101 and is connected to piston 105 to reciprocate the piston in cylinder 102. Various types of motors may be used in the practice of this invention, and the motor may be connected to support frame 101 in any acceptable way. Preferably, motor 106 is a conventional direct current motor including a speed reducing section and a rotatable output shaft 151, and the motor is bolted to back plate 111 of support frame 101 with the output shaft extending through opening 115.

Also, motor 106 may be connected to piston 105 in any suitable way. With the preferred embodiment of the invention shown in the drawings, motor shaft 151 is connected to drive rod 152, which may comprise a conventional drive screw, via a coupling member 155 that transmits rotary motion from the motor shaft to the drive screw. Drive screw 152 itself extends forward from coupling member 155 and includes a threaded forward portion that extends into and engages the threads of piston bore 147. With the above described arrangement, rotation of shaft 151 rotates drive rod 152; however, driving section 146 of piston 105 is prevented from rotating, and thus rotation of the drive rod against the threads of bore 147 forces the piston forward or rearward in cylinder 102, depending on the direction of rotation of the drive rod.

Cross-plate 156 is connected to and transversely extends across side section 107 to support and hold drive rod 152 and coupling member 155 in position. Plate 156 is located between retaining plate 131 and back plate 111, and preferably is slightly forward of coupling member 155. Central opening 157 is formed in plate 156, and the rear end of drive rod 152 extends into this opening. A bearing (not shown) may be located in opening 157 and directly engage and support the rear end of drive rod 152. Cross-plate 156 also forms a pair of outside openings through which support rods 35 and 136 extend.

Preferably, pump 100 further comprises auxiliary inlet means 160, shown in FIG. 2, to conduct additional fluid into fluid chamber 122 during operation of the pump; and this inlet means includes bore 161, connecting tube 162, and valve 165. Bore 161 is formed in and extends through side wall 125 of cylinder 102, in communication with fluid chamber 122. Connecting tube 162 has a first end located in bore 161 and extends outward therefrom, and valve 165 is connected to the connecting tube, for example to a second end thereof, to control the flow of fluid through the connecting tube. Preferably, valve 165 itself includes an inlet to connect the valve to a source of the additional fluid; and the valve has an open position for conducting fluid from this inlet to connecting tube 162, and a closed position to prevent fluid flow between the valve inlet and connecting tube. With this preferred arrangement, valve 165 further includes a control, such as a handle that may be moved by hand by an operator, to move the valve between its open and closed positions.

Control means are provided to control the direction, the distance and the speed of movement of piston 105 in cylinder 102 and hence the volume and the rate of fluid injected into and aspirated from the patient. This control means includes front detector 166, which generates a first signal when piston 105 reaches a predetermined forward position, and rear detector 167 which generates a second signal when the piston reaches a predetermined rearward position. The operation of these detectors and the way they cooperate to control movement of piston 105 are discussed in detail below. The structure of each of these detectors, though, is comprised of a U-shaped bracket having spaced first and second legs, radiation sensitive means located on tee first leg, and radiation generating means located on the second leg.

Front detector 166 is connected to support frame 101, specifically side wall 101a. With reference to FIG. 3, detector 166 is mounted on L-shaped plate 170, and screw 171 extends through side wall 101a and engages this plate to hold the plate securely against that side wall. Rear detector 167 is similarly connected to support frame 101, specifically side wall 101b, by means of L-shaped plate 172 and screw 173 that extends through side wall 101b into engagement with plate 172. Both detectors 166 and 167 are located rearward of and at a level below cylinder 102. Front detector 166 is located forward of rear detector 167, and the rear detector is located forward of cross-plate 156.

As shown in FIG. 2, side wall 101b forms elongated slot 175, and screw 173 extends through this slot to hold plate 172 against the side wall. The position of detector 167 may be changed by simply loosening screw 173, moving the screw, plate 172 and detector 167 along slot 175 to a new position, and then retightening screw 173 in this new position. A similar slot (not shown) is formed in side wall 101a to allow an easy adjustment of the position of plate 170 and detector 166. Pins 176 extend through slot 175 and into engagement with plate 172 to help hold that plate and detector 167 level inside support frame 101, and similar pins (not shown) may be likewise used to help hold plate 170 and detector 166 level inside the support frame.

Actuating means is mounted on piston 105 and actuates front and rear detectors 166 and 167 to generate the above-mentioned first and second signals. Preferably, this actuating means includes the previously discussed transversely extending bar 150, which is mounted on piston 105 and support rods 135 and 136, and a pair of plates or flags 177 and 178 that are connected to and extend downward from outward portions of bar 150. Plates 177 and 178 are positioned so that, first, when piston 105 reaches the above-mentioned predetermined forward position, plate 177 is located between the legs of front detector 166 to block the radiation sensitive means thereof from the radiation generating means of the first detector; and second, when the piston reaches the above-mentioned predetermined rearward position, plate 178 is located between the legs of rear detector 167 to block the radiation sensitive means thereof from the radiation generating means of the rear detector. A pair of bushings may be mounted on support rods 135 and 136, between those rods and bar 150, to facilitate sliding movement of the bar along the support rods.

An advantage of pump 100 of this invention is that cylinder 102 and head section 145 of piston 105, the parts of the pump that may come into direct contact with fluid injected into and aspirated from the body of the patient, can be easily removed and replaced. To do this, wing nuts 121 and 137 are removed and front plate 110 is pulled away from the front edges of side section 107. Cylinder 102 is pulled off piston 105 and removed from pump 100, and then head section 145 of the piston is threaded off driving section 146 and removed. Cylinder 102 and head section 145 may then be thoroughly cleaned and sterilized and replaced, or another cylinder and another piston head section may be installed in pump 100. With front plate 110, cylinder 102, and piston head section 145 removed, it is also very easy to remove sleeves 142, retaining plate 131 and piston driving section 146. To elaborate, sleeves 142 and retaining plate 131 may be removed by simply sliding these parts forward off support rods 135 and 136. Drive section 146 is removed by disconnecting it from bar 150 and then threading the driving section forward off drive rod 152.

To replace piston 105, retaining plate 131, sleeves 142, and cylinder 102, driving section 146 of the piston is threaded onto drive rod 152 and then connected to bar 150 so that this bar prevents rotation of the piston drive section. Retaining plate 131 is mounted on support rods 135 and 136 and slid rearward, against shoulders 141, and then sleeves 142 are mounted on the support rods and slid against the retaining plate. Head section 145 of piston 105 is threaded onto piston driving section 146 and then cylinder 102 is slid onto the piston With cylinder 102 and piston 105 in place, front plate 110 is then mounted on pins 120 and rods 135 and 136 as shown in FIGS. 1 and 2, and wing nuts 121 and 137 are threaded onto those pins and rods respectively, securely connecting the front plate to side section 107 and tightly holding the support rods between the front and back plates of support frame 101.

Pump 100 is especially well adapted to help dissolve solids in vivo by distributing and agitating a dissolving agent in a localized body area of a patient. For example, a dissolving agent such as mono-octanoin or methyl tertiary-butyl ether, is introduced into a localized area of a patient's body to dissolve undesirable solids such as gall stones or kidney stones that have formed in that body area. This dissolving agent may be introduced into the body by any suitable means e.g., catheter placement. Then, the tube or catheter is connected to pump 100, specifically connector 130. This tube or catheter may be inserted into the patient's body in any acceptable way such as through percutaneous transhepatic catheter placement, endoscopic retrograde biliary catheter placement, or placement of a T-tube into the localized area by surgical means. Pump 100 is activated to oscillate a fluid between chamber 122 and the localized area of the patient's body to distribute and agitate the dissolving agent therein, improving the rate at which that agent dissolves the undesirable concretions.

The oscillating fluid can be injected into the body area and aspirated therefrom at various rates, although it has been found that particularly good results may be obtained if the oscillating fluid is injected at a rate faster than the rate at which, and for a time period shorter than the time period over which, the fluid is aspirated from the body.

The same fluid used as the dissolving agent may be used as the oscillating or agitating fluid. Alternately, the agitating fluid may be a mixture of liquids that does or does not include the dissolving agent. Water, organic solvents, or solvents for the dissolving agent may also be used as or in the oscillating fluid.

It is normally desirable to maintain constant the volume of liquid injected into and aspirated from the body of the patient. Over time, however, oscillating fluid may be lost due to seepage from the body area or absorption into other body parts. If this happens, fluid may be added to fluid chamber 122 via auxiliary inlet 160, without stopping pump 100, to maintain an effective amount of the oscillating fluid therein. If the dissolving agent is used as the oscillating fluid, adding dissolving agent to fluid chamber 122 from time to time may also increase the effectiveness of the dissolving agent in vivo by replacing dissolving fluid that has been become inactive.

Pump 100 may be used to help dissolve many types of solids in vivo such as kidney and urinary tract stones, blockages in the digestive system, and intravascular blood clots, atherosclerotic cholesterol placques and other undesirable matter in the arterial system. When used to dissolve gallstones in vivo, it is important that a very carefully monitored volume, e.g. 5 ml, be rapidly infused through a small caliber catheter, e.g 1.7 mm external diameter, at a carefully controlled rate, and then more slowly, but completely, aspirated in a cyclical fashion. The rapid infusion requires a high pressure, carefully controlled system; and the slow, complete aspiration inhibits the introduction of air into the body area being treated either as the result of the development of a low pressure therein, or as the result of air leaking into pump 100. The infusion and retrieval of the oscillating fluid should be closely monitored to avoid excessive overflow of the fluid from the gallbladder and the absorption of that fluid into the body.

Also, pump 100 may be used to oscillate a fluid into and out of a localized body area for other purposes; for example, to distribute other antibiotics or cancer combatants throughout a localized or target area to enhance their surface contact or absorption. Further, pump 100 may be used to enhance the local efficacy of hydrophobic therapeutic agents which are poorly miscible or soluble in an aqueous body fluid such as bile.

During use of pump 100, it is possible that bile or stone debris may be aspirated from the body of the patient, and it is desirable that these materials not be reinjected into the patient's body. To prevent this, a trap may be used to collect such debris withdrawn from the patient, and FIGS. 4 and 5 shows a trap 180 that may be used with pump 100 to do this. Trap 180 comprises any suitable liquid collection vessel including a fluid inlet 181 and a fluid outlet 182; and in use, the trap is filled with the oscillating fluid, a first tube is used to connect pump 100 to the trap inlet, and a second tube is used to connect the patient's body to the trap outlet. As pump 10 forces fluid into trap 180, fluid therefrom is forced through outlet 182 and into the patient's body; and as the pump pulls fluid out from the trap, fluid is aspirated from the body of the patient back into the trap. Any solids or liquids aspirated from the patient that have a density greater than the density of the oscillating fluid, sink to the bottom of trap 182 and thus do not pass back through trap outlet 182 and are not recirculated back into the patient's body.

Preferably, trap 180 is provided with means for discharging debris from the trap without interrupting the operation of the trap or pump 100. With trap 180 shown in FIG. 4, this discharging means comprises a debris outlet 185 formed in the top of the trap, and debris discharge tube 186 that extends downward from this debris outlet into the lower portion of the trap. Air outlet 187, normally closed or covered during use of trap 180, is also provided in the top of the trap to vent from the trap air or other compressible vapor or gases that may collect in the trap.

Trap 180 includes collection chamber 188, cover 190 and base 191. Collection chamber 188 is held between cover 190 and base 191, which in turn are securely connected together by connecting rods 192 and wing nuts 193. Cover 190 extends across the top of collection chamber 188 and forms the above-mentioned inlet 181 and outlets 182, 185 and 187. Preferably, collection chamber 188 is made from a transparent material to allow visual inspection of the interior of that chamber, and rubber pad 196 is located between base 191 and the bottom of the collection chamber to cushion the lower end thereof. During the above-described operation of pump 100 and trap 180, a conventional pressure gauge (not shown) may be connected to the trap, in communication with the interior thereof, to show the fluid pressure therein and, hence, the fluid pressure in the interior of cylinder 102 of the pump.

FIG. 6 is a schematic diagram of an electric control circuit 200 for pump 100, and in particular for motor 106. Generally, circuit 200 includes switch means 200a and switch control means 200b. Switch means 200a has a first position or state actuating motor 106 to move piston 105 forward in cylinder 102, and a second position or state actuating the motor to move the piston rearward in the cylinder; and this switch means includes forward and rearward speed control means to vary, respectively, the forward and rearward speeds of the piston in fluid chamber 122 and, hence, the rate at which fluid is injected into and aspirated from the body area being treated. Switch control means 200b is provided to change switch means 200a from its first state to its second state when piston 105 reaches a predetermined forward position, and to change the switch means from its second state to its first state when the piston reaches a predetermined rearward position. With the embodiment of the control circuit shown in FIG. 6, switch means 200a includes controller 201, relay coils 202 and 205, and potentiometers 206 and 207; and switch control means 200b includes front detector 166, back detector 167, logic subcircuit 210 and stop-start subcircuit 211.

Controller 201 is a conventional motor control that governs the direction and speed of rotation of motor shaft 151 by controlling the polarity and magnitude of the voltage applied to the windings of motor 106, and this is done in response to the polarity and magnitude of the voltage applied to an input 201a of the controller, referred to as the command control input. Controller 201 has two output connections 201b and 201c that are connected to motor 106, and the controller provides +10 V and −10 V Direct Current potential sources. Controllers of this type are well known in the art and, for example, controller 201 may comprise controller model number E-352-B manufactured by the Motorcraft Company Inc.

Relay coil 202 includes a magnetic coil 202a and switch 202b. Switch 202b is normally open, and the switch closes when a current of sufficient magnitude is conducted through coil 202a. When this happens, switch 202b connects controller command input 201a to a −10 DC voltage source, via line 202c, so that piston 105 is pulled rearward in cylinder 102. A first end of coil 202 is connected to voltage source $E_1$, and a second end of this coil is connected to a first output connection of logic subcircuit 210, discussed in detail below. When this output connection of logic circuit 210 is at a high voltage level, current does not flow through coil 202a and switch 202b is open. However, when this first output connection of the logic subcircuit is at a low voltage level, a voltage difference exists across coil 202a; and this causes current to flow through that coil, closing switch 202b, and actuating motor 106 to move piston 105 rearward in cylinder 102. Variable potentiometer 206 is located in line 202c to vary the magnitude of the voltage applied to controller command input 201a when switch 202b is closed and, in this way, the speed at which motor 106 pulls 202b piston 105 rearwardly and the rate at which the piston aspirates fluid from the patient.

Relay coil 205, similar to relay coil 202, includes magnetic coil 205a and switch 205b. Switch 205b is normally open, and the switch closes when a current of sufficient magnitude is conducted through coil 205a. When this happens, switch 205b connects controller command input 201a to a +10 DC voltage source, via line 205c, and this causes the controller to actuate motor 106 so that piston 105 is pushed forward in cylinder 102. A first end of coil 205a is connected to a voltage source $E_2$, and a second end of this coil is connected to a second output connection of logic subcircuit 210. When this output connection of logic subcircuit 210 is at a high voltage level, current does not flow through coil 205a, and switch 205b is open. When this second output connection of logic subcircuit 210 is at a low voltage level, however, a voltage difference exists across coil 205a; and this causes current to flow through that coil, closing switch 205b and actuating motor 106 to move piston 105 forward in cylinder 102.

Variable potentiometer 207 is located in line 205c to vary the magnitude of the voltage applied to controller command input when switch 205b is closed and, thereby, the speed at which the motor pushes piston 105 forward and the rate at which the fluid in pump 100 is injected into the patient. By providing separate potentiometers 206 and 207, each one controlling the speed of piston 105 in a different direction, the speeds at which the piston moves forward and rearward in cylinder 102 and the rate at which the fluid is injected into and aspirated from the patient can be controlled separately and independently.

Switch control means 200b controls the operation of relay coils 202 and 205 in response to, first, signals generated by front and rear detectors 166 and 167, and second, a signal generated by stop-start subcircuit 211.

Front detector 166 includes radiation emitting diode 166a, radiation sensitive transistor couple 166b, and output connection 166c. Diode 166a is electrically located in line 166d between voltage source $E_3$ and ground, transistor couple 166b is electrically located in line 166e between voltage source E and ground, and output connection 166c is also located in line 166e between voltage source $E_3$ and transistor couple 166b. A 500k resistor is located in line 166d to limit the current through diode 166a; and a 10k resistor is located in line 166e, between voltage source $E_3$ and output connection 166c, to insure a voltage drop across that portion of line 166e.

In the absence of the appropriate radiation, transistor couple 166b is nonconductive, in effect acting as an open switch in line 166e; and when the transistor couple is in this state, output point 166c of detector 166 has relatively high potential such as one or two volts. However, when radiation having a sufficient intensity in a predetermined wavelength range strikes base 166f of transistor couple 166b, the transistor couple is rendered conductive, in effect acting as a closed switch in line 166e; and when the transistor couple is in this state, the voltage potential of point 166c drops to a low potential such as zero volts. Diode 166a is provided to selectively render transistor couple 166b conductive. To elaborate, diode 166a and transistor couple 166b are physically located on opposite legs of U-shaped bracket 166g, with the diode immediately opposite and closely adjacent base 166f of the transistor couple. When current from voltage source $E_3$ passes through diode 166a, the diode emits radiation that, unless blocked, strikes base 166f of transistor couple 166b and causes that transistor couple to become conductive.

In the operation of pump 100, normally base 166e of transistor couple 166a is not blocked from the radiation emitted by diode 166a, and the transistor couple is conductive and point 166c is at a low voltage potential. However, when piston 105 reaches a predetermined forward position in cylinder 102, plate 177 is pulled between diode 166a and transistor couple 166b, blocking the latter from the radiation emitted by the former. This renders transistor couple 166b nonconductive, bringing point 166c to a relatively high voltage level.

Back detector 167 includes diode 167a, transistor couple 167b, output connection 167c, lines 167d and 167e, and transistor base 167f. The various elements of detector 167 are arranged and operated in a manner substantially identical to the way the corresponding elements of detector 166 are arranged and operated. The principal differences between detectors 166 and 167 are that they are physically located on different U-brackets and are employed to sense different positions of piston 105. Also, diode 167a and transistor couple 167b are connected to voltage sources $E_5$ and $E_6$ respectively.

During use of pump 100, normally, base 167f of transistor couple 167b is not blocked from the radiation of diode 167a, and the transistor couple is conductive and point 167c is at a low voltage potential. When piston 105 reaches a preset rearward location in cylinder 102, plate 178 is pulled between diode 167a and transistor couple 167b, blocking the latter from the radiation emitted by the former. This causes transistor couple 167b to become nonconductive, raising the voltage level of point 167c to a relatively high level. While various types of transistor couples may be used in the practice of this invention, preferably transistor couples 166b and 167b are of a type that are rendered conductive by electromagnetic radiation in the infrared frequency range, and of course diodes 166a and 167a are of a type that emit such radiation.

Logic subcircuit 200 is electrically located between relay coils 202 and 205, on the one hand, and detectors 166 and 167 on the other hand; and this subcircuit includes flip flop 212, two nand gates 215 and 216, and two voltage inverters 217 and 220.

Flip flops, such as flip flop 212, of circuit 200, are electronic devices having a plurality of inputs and outputs, and a number of useful characteristics. First, flip flops have a pair of output connections or signals that maintain an opposite relationship—when one of these output connections has a high voltage potential, the other output connection has a low voltage potential, and vise versa. Second, flip flops can be constructed so that, if certain input and output conditions are present, the output connections change whenever either input connection changes; but, if certain other input and output connections are present, a single change in the input conditions has no affect on the output conditions.

Flip flop 212 of circuit 200 has two input connections 212a and 212b and two output connections 212c and 212d. Input connection 212a is connected to output connection 166c of detector 166 via line 221; and voltage inverter 217 is located in this line so that when detector output connection 166c has a high voltage level, flip flop input connection 212a has a low voltage level, and when detector output connection 16c has a low voltage level, flip flop input connection 212a has high voltage level. Input connection 212b is connected to output connection 167c of detector 167 via line 222; and voltage inverter 220 is located in this line so that when detector output connection 167c has a high voltage level, flip flop input connection 212b has a low voltage level, and when detector output connection 167c has a low voltage level, flip flop input connection 212b has a high voltage level.

FIG. 7 summarizes the operation of flip flop 212. When both input connections 212a and 212b are at a high voltage potential, if either one of these input connections changes to a low voltage potential, then each output connection 212c and 212d of the flip flop changes either from a high voltage potential to a low voltage potential or vise versa. However, when one of input connections 212a and 212b is at a high voltage potential and the other input connection is at a low voltage connection, then a single change in the voltage level of either one of these input connections has no affect on the voltage potentials of output connections 212c and 212d.

Nand gates, such as gates 215 and 216 of circuit 200, are electronic logic device having two input connections and one output connection, and FIG. 7 summarizes their operation. The output connection of a nand gate has a low voltage potential only when both input connections have a high voltage potential. Otherwise, the output of a nand gate has a high voltage potential.

Input connections 215a and 216a of nand gates 215 and 216 are connected to output connections 212c and 212d respectively of flip flop 212. In this way, input connections 215a and 216a are always at different voltage levels—when the former connection is at a high voltage potential, the latter connection is at a low voltage potential, and vise versa. Input connections 215b and 216b of nand gates 215 and 216 are connected to stop-start subcircuit 211, discussed below. Output connection 215c of the nand gate 215 forms the above-mentioned first output connection of logic subcircuit 210 and is connected to relay coil 202, and output connection 216c of nand gate 216 forms the above-mentioned second output connection of the logic subcircuit and is connected to relay coil 205.

Stop-start subcircuit 211 is provided to initiate and terminate movement of piston 105 in cylinder 102; and this subcircuit includes flip flop 225, start and stop buttons, identified as START and STOP respectively in FIG. 6, detector error sensor section 226, and safety sensor section 227.

Flip flop 225 has three inputs and two outputs. A first input 225a of flip flop 225, referred to as the data input, is connected to voltage source $E_7$ which maintains the data input of the flip flop at a high voltage level. START switch is connected to a second input 225b of flip flop 225, referred to as the clock input, via line 200; and detector error sensor section 226, safety sensor section 227, and STOP switch are all connected to a third input 225c of the flip flop, referred to as the reset input, via line 231. Only one of the outputs of flip flop 225 is used in circuit 200, and this output 225d is connected to inputs 215b and 216b of nand gates 215 and 216.

FIG. 8 summarizes the operation of flip flop 225. As can be seen, when the voltage level of reset connection 225c is at a low voltage level, output connection 225d is also at a low voltage level. However, when reset connection 225c is at a high voltage level, the voltage level of data input connection 225a is transferred to output connection 225d when the START switch is closed and then opened. When output connection 225d is at a high voltage level, it will stay at that level until either data input connection 225a or reset connection 225c drop to a low voltage level, at which time the output connection 225d also falls to a low voltage level. Thus, with the arrangement of this invention, where data input connection 225a is kept at a high voltage level, output connection 225d will switch from a high voltage level to a low voltage level, if and only if reset connection 225c assumes a low voltage level.

When output connection 225d of flip flop 225 is at a high voltage level, the voltage levels of one or the other of output connections 215c and 216c is at a low voltage level Thus, motor 106 is operating, with the direction of movement of piston 105 being determined by which Nand gate output connection has the low voltage potential, and this in turn is determined by which of the outputs of flip flop 212 has a high voltage level. However, when output connection 225d of flip flop 225 is at a low voltage level, output connections 215c and 216c of Nand gates 215 and 216 are both at a high voltage level, regardless of the voltage levels of input 215a and 216a of the Nand gates. Thus, motor 106 is deactivated regardless of the voltage levels of output connections 215c and 216c of flip flop 212.

START switch is used to start pump 100, and specifically, motor 106. To elaborate, when motor 106 is not operating, output connection 225d of flip flop 225 is at a low voltage level, and START switch is employed to bring input connection 225b of the flip flop temporarily to a low voltage level to change the output connection 225d to a high voltage level. START switch is located between an end of line 230 and ground, and voltage source $E_8$ is also connected to line 230 at point 230a, via line 232. A 10k resistor (not shown) is located in line 232 to insure a voltage drop thereacross. Normally, START switch is open, and the voltage level at points 230a and 225b is at a relatively high level. However, when START switch is closed, the switch shunts current from the voltage source $E_8$ to ground, bringing the voltage level at point 225b to a low voltage level, approximately zero.

Detector error sensor section 226, safety sensor section 227, and STOP switch are used to stop pump 100, either automatically upon the occurrence of a predetermined condition, or at the will of an operator. More specifically, when motor 106 is operating output connection 225d of flip flop 225 is at a high voltage level, and detector error sensor section 226, safety section 227, and STOP switch may be employed to bring input connection 225c of the flip flop to a low voltage level to change the output connection 225d thereof to a low voltage level.

Detector error sensor section 226 is connected to line 231 at point 231a, safety sensor section 227 is connected to line 231 at point 231b, and stop switch is connected to line 231 at point 231c. Voltage source $E_9$ is also connected to line 231, with points 231a, 231b, and 231c located in series in line 231 between voltage source $E_9$ and input 225c of flip flop 225. A 10k resistor is located in line 231, between voltage source $E_9$ and point 231a, to insure a voltage drop across this portion of line 231, and the voltage level at input 225c of flip flop 225 normally is maintained by voltage source $E_9$ at a relatively high level. However, if the voltage level of any one of points 231a, 231b or 231c falls to a low level, then the voltage level at flip flop input 225c also falls to a low voltage potential.

Detector error sensor section 226 stops operation of pump 100 in case detector output connections 166c and 167c are both at a high voltage potential at the same time, a condition that should not occur during normal operation of the pump. Detector error sensor section 226 comprises nand gate 235, which has two input connections 235a and 235b and an output connection 235c. Input 235a is connected to output 166c of detector 166 via line 236 so that the voltage levels of points 235a and 166c are the same; and, similarly, input 235b is connected to output 167c of detector 167 via line 237 so that connections 235b and 167c are at the same voltage level. With reference to FIG. 7, output connection 235c of nand gate 235 has a high voltage level unless both input connections are at a high voltage level, in which case the output connection of the nand gate has a low voltage level. When this happens input 225c of flip flop 225 also falls to a low voltage level.

Safety sensor section 227 senses a parameter such as the fluid pressure in cylinder 102 and stops operation of pump 100 in case the value of the sensed parameter moves outside a desired range; and this section of circuit 200 comprises comparator 240, variable potentiometer 241, and sensor 242, Comparator 240 has two inputs 240a and 240b and one output 240c; and if the voltage level at input 240a is greater than the voltage level at input 240b, then output connection 240c is at a high voltage level; however, if the voltage level of input 240b rises above the voltage level of input 240a, then the voltage level of output connection 240c drops to approximately zero.

Potentiometer 241 is located in line 245, between voltage source $E_{10}$ and ground, and the potentiometer is connected to and determines the voltage level of input 240a of comparator 240. Sensor 242 may be any suitable sensor that produces an electric voltage potential indicative of a particular parameter, and the sensor is connected to and determines the voltage level of input 240b of comparator 240. For instance, sensor 242 may be a pressure transducer that is connected to a fluid line that, in turn, is connected to the interior of cylinder 102, for example via valve 165, such that the sensor is subject to, and produces an electric potential corresponding to, the fluid pressure inside cylinder 102. Other parameters may be sensed, however; and in fact, with modifications well within the ability of one of ordinary skill in the art, circuit 200 may be designed to sense a multitude of parameters simultaneously and to stop pump 100 in case any one of the sensed parameters falls outside a predetermined range.

With the above-described arrangement, as long as the value of the sensed parameter stays in a predetermined range, output connection 240c of comparator 240 has a high voltage level, but when that sensed parameter moves outside the predetermined range, the output connection of the comparator drops to a low voltage level. This predetermined range of the sensed parameter, and specifically the value thereof at which output 240c of comparator 240 changes from high voltage level to a low voltage level, may be adjusted by changing the value of potentiometer 241.

STOP switch is located in line 246 between point 231c and ground, and normally the stop switch is open, blocking current flow through line 246. However, if the STOP switch is closed, the switch connects point 231c to ground, bringing the electric potential of that point and input 225c connection of flip flop 225 to a zero potential.

The operation of pump 100 and circuit 200 will be clear to those of ordinary skill in the art from a review of the above discussion. Nevertheless, that operation will be summarized below.

When pump 100 is deactivated, piston 105 is at rest, START and STOP switches are both open, and output connection 225d of flip flop 225 is at a low voltage level. The specific positions of piston 105 and plates 180 and 181 depend on where the piston was last stopped in pump 100, and the specific condition of flip flop 212 depends on where the piston is and the direction in which the piston was moving when it was last stopped. For the sake of discussion, piston 105 will be considered to be in the position shown in FIG. 1, and flip flop 212 will be considered to be in condition number 3 of FIG. 7. Thus plates 180 and 181 are spaced from detectors 166 and 167, both transistor couples 166b and 167b are conductive, and points 166c and 167c are at a low voltage level. Output 212c of flip flop 212 and input 215a of nand gate 215 are both at a high voltage level, and output 212d of the flip flop and input 212b of nand gate 216 are both at a low voltage level. However, inputs 215b and 216b of nand gates 215 and 216 are both at a low voltage potential because of their connection to flip flop 225. Consequently, nand gate outputs 215c and 216c are both at a high voltage level, and switches 202b and 205b are both open.

To start pump 100, START switch is momentarily closed and then opened. This causes output connection 225d of flip flop 225 to change to a high voltage level, and this brings both input connections 215b and 216b of nand gates 215 and 216 to a high voltage level, in effect transferring control of switches 202b and 205b to flip flop 212. Since input connections 215a and 216a are at high and low voltage potentials respectively, output connection 215c of nand gate 215 changes to a low voltage level when input connection 215b changes to a high voltage level. Current is conducted through relay coil 202 and to control input 201a via switch 202b, and motor 106 is actuated to pull piston 105 rearward in cylinder 102, with the speed of the piston determined by potentiometer 206. Output connection 216c of nand gate 216 remains at a high voltage level because input connection 216a thereof is at a low voltage level, and switch 205b remains open.

Piston 105 continues to move rearward until plate 178 moves between the legs of bracket 167g, When this occurs, plate 181 blocks transistor couple 167b from the light of diode 167a, and the transistor couple is rendered nonconductive. This changes the voltage at point 167c from a low to a high level, and input 212b of flip flop changes from a high voltage level to a low voltage level. This causes the voltage levels of flip flop outputs 212c and 212d to flip, and specifically, the former point changes to a low voltage potential and the latter point changes to a high voltage potential. Now, the voltages of nand gate inputs 215a and 216a flip to high and low levels respectively, and the voltages of nand gates outputs 215c and 216c change to high and low levels respectively. With these voltages, current stops flowing through relay coil 202 and starts to pass through relay coil 205, opening switch 202b and closing switch 205b. Current is conducted to controller command input 201a via switch 205b, and motor 106 is operated to push piston 105 forward in cylinder 102.

As piston 105 moves forward, plate 178 pulls away from bracket 167g, and radiation from diode 167a renders transistor couple 167b conductive. This causes the voltages at points 167c and 212b to change to low and high levels respectively. Nevertheless, as shown FIG. 7, this change in the voltage level of point 212b of flip flop 212 does not affect the voltage level of output connections 212c and 212d of the flip flop. The voltage level of the input and output connections of nand gates 215 and 216 remain unchanged, switch 202b remains open, switch 205b remains closed and piston 105 continues to move forward.

Piston 105 continues to move forward in cylinder 102, until plate 177 comes between the legs of bracket 166g and blocks the radiation of diode 166a from base 166f of transistor couple 166b. When this happens, transistor couple 166b becomes nonconductive, and the voltage at point 166g changes to a high level, and the voltage at flip flop input connection 212a changes to a low level. This change in the voltage level at input connection 212a of flip flop 212 causes voltage levels of outputs 212c and 212d to flip—the voltage of the former output connection increases to a high level and the voltage of the latter output connection falls to a low level. As a result, the voltages at input connections 215a and 216a of nand gates 215 and 216 also change to high and low levels respectively. The voltage of output connection 216c of nand gate 215 changes to a low level, and the voltage of output connection 216c of nand gate 216 changes to a high level. Current stops flowing through relay coil 205 and switch 205b opens, and current begins to conduct through relay coil 202 so that switch 202b is closed. Current is now conducted to controller command input via line 202c, causing motor 106 to pull piston 105 rearward in cylinder 102.

As piston 105 moves rearward, plate 177 moves away from bracket 166g, and radiation from diode 166a causes transistor couple 166b to become conductive. This changes the voltage at point 166c to a low level and the voltage at input 212a of flip flop 212 to a high level. The voltages of output connections 212c and 212d of flip flop 212 remain the same, however, as shown in FIG. 7. The voltage levels of the input and output connections of nand gates 215 and 216 are unchanged, switch 202b stays closed, switch 205b remains open, and piston 105 continues to move rearward.

Preferably, back-up means comprising forward and rearward limit switches 246 and 247 and voltage sources $E_{11}$ and $E_{12}$ is provided to reverse movement of piston 105 if detectors 166 and 167 do not do so. Forward limit switch 246 is connected to support frame 101, forward of front detector 166 and at a height level with bar 150, and this limit switch is electrically located in line 221 between the front detector and inverter 217. Voltage source $E_{11}$ is also connected to line 221 via point 221a, between switch 246 and inverter 220. As piston 105 moves forward in cylinder 102, if detector 166 does not reverse movement of the piston, continued forward movement of the piston causes bar 150 to contact and open switch 246. This disconnects flip flop 212 from transistor couple 166b and voltage source $E_4$; however, voltage source $E_{11}$ remains connected to line 221 and causes point 221a to assume a high voltage level. Inverter 217 causes a low voltage to be applied to flip flop input 212a, causing motor 106 to reverse the direction of movement of piston 105.

Rearward limit switch 247 is connected to support frame 101, rearward of rear detector 167 and at a height level with bar 150, and this limit switch is electrically located in line 222 between the rear detector and inverter 220. Voltage source $E_{12}$ is also connected to line 222 via point 222a, between switch 247 and inverter 217. As piston 105 moves rearward in cylinder 102, if detector 167 does not reverse movement of the piston, continued rearward movement of the piston causes bar 150 to contact and open switch 247. This disconnects flip flop 212 from transistor couple 167b and voltage source $E_6$; however, voltage source $E_{12}$ remains connected to line 222 and causes point 222a to assume a high voltage level. Inverter 220 causes a low voltage to be applied to flip flop input 212b, causing motor 106 to reverse the direction of movement of piston 105.

Movement of piston 105 is stopped when the voltage of input connection 225c of flip flop 225 falls to a low level. As previously discussed, this occurs if STOP switch is closed or if the voltages at either points 231a or 231b falls to a low level. If one of these three events occurs, the voltage of output 225d of flip flop 225 and thus the voltages of inputs 215b and 216b of nand gates 215 an 216 change to low voltage levels, in effect taking control of switches 202b and 205b away from flip flop 212—that is, since inputs 215b and 216b are at low voltage levels, outputs 215c and 216c of nand gates 215 and 216 are at high voltage levels regardless of the voltage levels of nand gate inputs 215a and 216a. Current is prevented from passing through either coil 202a and 205a, and both switches 202b and 205b are open. Motor 106 is deactivated, and piston 105 is stopped in cylinder 102.

As will be understood by those of ordinary skill in the art, any suitable voltage sources may be used for $E_1$–$E_{12}$, and these voltage sources may all be connected to one primary source. With the preferred embodiment of circuit 200, the logic devices used in the circuit require that sources $E_1$–$E_{12}$ each provides a +5 DC voltage potential, although circuit 200 may be modified to use voltage sources of a different magnitude. Also, suitable energy sources (not shown) are provided for the electronic elements of circuit 200 including flip flops 212 and 225, inverters 217 and 220, Nand gates 215; 216 and 235, and comparator 240.

While it is apparent that the invention herein disclosed is well calculated to fulfill the objects previously stated, it will be appreciated that numerous modifications and embodiments may be devised by those skilled in the art, and it is intended that the appended claims cover all such modifications and embodiments as fall within the true spirit and scope of the present invention.

What is claimed is:

1. A pump for directing a fluid into and out from a body area, the pump comprising:
   a support frame including
   (i) a side section forming a front opening,
   (ii) a front plate extending across the front opening and forming a pump inlet, and
   (iii) means releasably connecting the front plate to the side section;
   a cylinder for holding the fluid, located within the support frame and forming a fluid chamber in communication with the pump inlet;
   a piston extending into the fluid chamber and supported for forward and rearward reciprocating movement therein, to inject fluid outward from the fluid chamber and into the body area and to aspirate fluid from the body area and inward into the fluid chamber;
   power means supported by the frame and connected to the piston to reciprocate the piston in the fluid chamber;
   means releasably connecting the cylinder to the support frame including
   (i) support means longitudinally extending rearward from the front plate, and
   (ii) a retaining plate supported by the support means, transversely extending across the cylinder, rearward thereof, and capturing the cylinder between the front plate and the retaining plate.

2. A pump according to claim 1 wherein: the support means includes first and second support rods extending rearward from the front plate;
   the retaining plate is mounted on the support rods; and
   the support means further includes means limiting longitudinal movement of the retaining plate on the rods.

3. A pump according to claim 2 wherein the limiting means includes:
   a shoulder formed on one of the rods rearward of the retaining plate to limit rearward movement thereof; and
   a spacing sleeve mounted on one of the rods, forward of retaining plate, to limit forward movement thereof.

4. A pump according to claim 3 wherein:
   the support frame further includes a back plate connected to a back end of the side section;
   the rods are connected to the back plate, extend forward therefrom, through the front plate, and have front ends located forward thereof; and
   the support means further includes means releasably mounted on the front ends of the rods, forward of the front plate, to hold the rods tightly extending between the front and back plates.

5. A pump according to claim 1 wherein:
   the piston forms a threaded bore; and the power means includes
   (i) a rotatable shaft, and
   (ii) a drive rod connected to the shaft for rotation therewith;
   the drive rod includes a threaded forward portion extending into engagement with the threaded bore; and
   the pump further includes means limiting rotation of the piston;
   whereby rotation of the drive rod reciprocates the piston to inject fluid into and aspirate fluid from the body 6. A pump according to claim 1 further comprising control means to control movement of the piston, the control means including:
   a front detector for generating a first signal;
   a rear detector for generating a second signal; and
   actuating means connected to the piston and actuating the front detector to generate the first signal when the piston reaches a first forward position, and actuating the rear detector to generate the second signal when the piston reaches a first rearward position.

7. A pump according to claim 6 wherein:
   the support frame includes a front plate;
   the means connecting the cylinder to the support frame includes support means longitudinally extending rearward from the front plate;
   the actuating means includes a bar mounted on the piston;
   the support means engage the bar to guide longitudinal movement thereof.

8. A pump according to claim 6 wherein: the front and rear detectors each includes
   (i) a U-shaped bracket having spaced first and second legs,
   (ii) a light sensitive means located on the first leg, and
   (iii) light generating means located on the second leg; and
   the actuating means includes plate means supported for movement between a first position, wherein the plate means extends between the legs of the front detector to block the light sensitive means thereof from the light generating means of the front detector, and a second position, wherein the plate means extends between the legs of the rear detector to block the light sensitive means thereof from the light generating means of the rear detector.

9. A pump according to claim 6 wherein the control means includes:
   a logic sub-circuit controlling the direction of movement of the piston;
   a first line connecting the logic sub-circuit to the front detector;
   a second line connecting the logic sub-circuit to the rear detector;
   a forward limit switch actuated by the actuating means to disconnect the logic subcircuit from the front detector when the piston reaches a second forward position, forward of the first forward position; and
   a rear limit switch actuated by the actuating means to disconnect the logic sub-circuit from the rear detector when the piston reaches a second rearward position, rearward of the first rearward position.

10. A pump according to claim 1 further comprising auxiliary pump inlet means to conduct additional fluid into the fluid chamber during operation of the pump.

11. A pump according to claim 10 wherein:
the cylinder includes a side wall extending around the fluid chamber; and the auxiliary inlet means includes
(i) a bore formed in and extending through the side wall, in communication with the fluid chamber,
(ii) a connecting tube having a first end located in the bore and extending outward therefrom, and
(iii) a valve connected to the connecting tube to control the flow of fluid therethrough.

12. A pump according to claim 11 wherein:
the valve means includes an inlet to connect the valve to a source of the additional fluid;
the valve has an open position for conducting fluid from the inlet thereof to the connecting tube, and a closed position to prevent fluid flow between the valve inlet and the connecting tube; and
the valve further includes a control to move the valve between the open and closed positions.

* * * * *

UNITED STATES PATENT AND TRADEMARK OFFICE
CERTIFICATE OF CORRECTION

PATENT NO. : 4,793,776

DATED : December 27, 1988

INVENTOR(S) : Johnson L. Thistle, et al.

It is certified that error appears in the above-identified patent and that said Letters Patent is hereby corrected as shown below:

Column 1, line 68: "mean" should read as --means--

Column 2, line 6: "draw" should read as --drawn--

Column 5, line 1: "35" should read as --135--

Column 5, line 36: "tee" should read as --the--

Column 6, line 48: "piston" should read as --piston.--

Column 8, line 4: "10" should read as --100--

Column 9, line 18: "202" should read as --202a--

Column 10, line 8: "E" should read as --$E_4$--

Column 11, line 7: "200" should read as --210--

Column 11, line 33: "16c" should read as --166c--

Column 11, line 57: "device" should read as --devices--

UNITED STATES PATENT AND TRADEMARK OFFICE
CERTIFICATE OF CORRECTION

PATENT NO. : 4,793,776
DATED : December 27, 1988
INVENTOR(S) : Johnson L. Thistle, et al.

It is certified that error appears in the above-identified patent and that said Letters Patent is hereby corrected as shown below:

Column 12, line 20: "200" should read as --230--

Column 12, line 48: "level" should read as --level.--

Column 15, line 12: "167g," should read as --167g.--

Column 15, line 48: "166g" should read as --166c--

Column 17, line 4: "215;" should read as --215,--

Column 17, line 33, Claim 1: "chamber;" should read as --chamber; and--

Column 18, line 13, Claim 5: "body" should read as --body area--

Signed and Sealed this

Tenth Day of October, 1989

Attest:

DONALD J. QUIGG

Attesting Officer

Commissioner of Patents and Trademarks